US00PP16858P3

(12) United States Plant Patent
Zaiger et al.

(10) Patent No.: US PP16,858 P3
(45) Date of Patent: Jul. 25, 2006

(54) NECTARINE TREE NAMED: 'POLAR LIGHT'

(50) Latin Name: ***Prunus persica* var. *nucipersica***
Varietal Denomination: Polar Light

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 169 days.

(21) Appl. No.: 11/011,970

(22) Filed: Dec. 15, 2004

(65) Prior Publication Data

US 2006/0130197 P1 Jun. 15, 2006

(51) Int. Cl.
*A01H 5/00* (2006.01)

(52) U.S. Cl. ..... Plt./188

(58) Field of Classification Search ..... Plt./188
See application file for complete search history.

*Primary Examiner*—Anne Marie Grunberg
*Assistant Examiner*—June Hwu

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA hardiness Zone 9, near Modesto, Calif., with standard commercial fruit growing practices, such as pruning, thinning, spraying, irrigation and fertilization. Its novelty consist of the following combination of desirable features:

1. Having a low winter chilling requirement of approximately 250 hours at or below 45° F.
2. Fruit ripening in the early maturity season.
3. Producing firm, white-fleshed fruit with very good flavor and eating quality.
4. A heavy and regular bearer of large fruit.
5. Fruit holding firm on the tree 8–10 days after maturity.
6. Vigorous and upright growth of tree.

1 Drawing Sheet

BACKGROUND OF THE VARIETY

Field of the Invention

In the field of plant genetics, we conduct an extensive and continuing plant-breeding program, including the organization and asexual reproduction of orchard trees, and of which plums, peaches, nectarines, apricots, cherries and interspecifics are exemplary. It was against this background of our activities that the present variety of nectarine tree (*Prunus persica* var. *nucipersica*), was originated and asexually reproduced by us in our experimental orchard located near Modesto, Stanislaus County, Calif.

Prior Varieties

Among the existing varieties of nectarine and peach trees, which are known to us, and mentioned herein, 'May Crest' Peach (U.S. Plant Pat. No. 4,064), 'May Glo' Nectarine (U.S. Plant Pat. No. 5,245), 'Tasty Gold' Nectarine (U.S. Plant Pat. No. 5,623) and 'Royal Glo' Nectarine (U.S. Plant Pat. No. 8,281).

ORIGIN OF THE VARIETY

The new and distinct variety of nectarine tree (*Prunus persica* var. *nucipersica*) was developed by us in our experimental orchard from seed of an open pollinated nectarine seedling which originated from a cross between selected proprietary parents with field identification numbers 172LE506 and 201LF103. The maternal parent (172LE506) originated from crosses between 'May Glo' Nectarine (U.S. Plant Pat. No. 5,245), 'Tasty Gold' Nectarine (U.S. Plant Pat. No. 5,623) and the proprietary selection '55G815'. The paternal parent (201LF103) originated from crosses between the following selections and varieties 'Royal Glo' Nectarine (U.S. Plant Pat. No. 8,281), 'May Crest' Peach (U.S. Plant Pat. No. 4,064), and the proprietary selection '43G1018'. A large number of these open pollinated nectarine seedlings were grown and budded to older trees of 'Nemaguard' Rootstock (non-patented), to accelerate rapid fruit production for evaluation. Under close and careful observation we recognized the desirable fruit characteristics of the present nectarine variety and selected it in 2002 for additional asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus persica* var. *nucipersica*) is of large size, vigorous, upright growth and a productive and regular bearer of large, firm, white-fleshed fruit with very good flavor and eating quality. The fruit is further characterized by ripening in the early maturity season, having good handling and shipping quality, the flesh being moderately juicy with a mild, sweet, low-acid flavor. The skin color having a yellow-white ground color overspread with an attractive orange-red blush and the size of the fruit being relatively uniform throughout the tree. The tree having a relatively low winter chilling requirement of approximately 250 hours at or below 45° F. In comparison to the low chilling parent 'May Glo' Nectarine (U.S. Plant Pat. No. 5245), the new variety is slightly larger in size, has white flesh compared to yellow flesh, requires approximately 50 hours less winter chilling, and is approximately 6 days earlier in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 5 year old specimens grown near Modesto, Calif., with color in accordance with Munsell Book of Color.

Tree:

*Size.*—Large, normal for most varieties of nectarine trees. The spread varies depending on cultural practice and average about 10'. Pruned to 3 to 3½ meters in height for economical harvesting of fruit.

*Vigor.*—Vigorous, growth of 1.5 to 2 meters the first growing season. Varies slightly with fertility, type of soil and climatic conditions.

*Form.*—Upright, usually pruned to vase shape.

*Branching habit.*—Upright, crotch angle approximately 30°, increases with heavy crop load.

*Productivity.*—Productive. Normal fruit thinning and spacing necessary for desirable market size fruit. Fruit set varies with climatic conditions during bloom time.

*Bearer.*—Regular, adequate fruit set 3 consecutive years. No alternate bearing observed.

*Fertility.*—Self-fertile.

*Density.*—Medium dense. Pruning to open center of tree to vase shape desirable to enhance fruit color and keep fruit wood healthy.

*Hardiness.*—Hardy in all stone fruit growing areas of California. Winter chilling requirement approximately 250 hours at or below 45° F. Grown in USDA Hardiness Zone 9.

Trunk:

*Size.*—Medium to large. Average 51.1 cm in circumference at 25 cm above ground on a 5 year old tree.

*Stocky.*—Medium stocky.

*Texture.*—Medium shaggy, roughness increases with age of tree.

*Color.*—Varies from 7.5YR 5/2 to 7.5YR 3/4.

Branches:

*Size.*—Medium. Average circumference 20.7 cm at 1.3 meters above ground.

*Surface texture.*—New growth smooth, becomes medium rough with age.

*Lenticels.*—Average number 28 in a 25.8 square cm area. Average length 2.4 mm. Average width 1.6 mm. Color varies from 5YR 6/8 to 5YR 5.8.

*Color.*—New growth varies from 5GY 6/6 to 10R 4/4 where exposed to sunlight. Old growth varies from 7.5YR 4/4 to 7.5YR 3/4.

Leaves:

*Size.*—Large. Average length 145.7 mm. Average width 41.4 mm.

*Form.*—Lanceolate.

*Apex.*—Acuminate.

*Base.*—Cunate.

*Margin.*—Crenate.

*Thickness.*—Medium.

*Surface texture.*—Upper surface relatively smooth, slightly indented over midrib and leaf veins. Lower surface relatively smooth with small ridges created by midrib and pinnate venation. Both surfaces glabrous.

*Petiole.*—Size — medium. Average length 10.2 mm. Average width 1.4 mm. Surface glabrous. Longitudinally grooved. Color 2.5GY 6/6.

*Glands.*—Reniform. Size — medium to large. Average length 1.5 mm. Average diameter 0.9 mm. Number varies from 2 to 4, average number 3. Located primarily on upper portion of petiole and base of leaf blade. Color 5R 4/6.

*Color.*—Upper surface varies from 2.5GY 4/6 to 5GY 5/6. Lower surface varies from 5GY 6/4 to 5GY 5/4. Midrib color varies from 2.5GY 8/4 to 2.5GY 7/4.

Flower buds:

*Size.*—Medium to large. Average length 15.5 mm. Average diameter 8.6 mm.

*Hardiness.*—Hardy in all stone fruit growing areas of California. Grown in USDA Hardiness Zone 9.

*Form.*—Conical, becoming elongated before opening.

*Pedicel.*—Average length 3.8 mm. Average width 1.1 mm. Color varies from 2.5GY 7/6 to 5GY 7/6.

*Color.*—Varies from 7.5RP 6/12 to 5RP 8/6.

Flower:

*Size.*—Large, showy. Average height 17.6 mm. Average diameter 25.7 mm.

*Petals.*—Number 5, alternately arranged to sepals. Form varies from elliptic to orbicular. Average length 15.9 mm. Average width 14.8 mm. Margin — sinuate, slightly cupped. Color varies from 7.5RP 9/2 to 5RP 7/8, fades with age of flower.

*Sepals.*—Number 5, alternately arranged to petals. Shape — ovate, apex rounded. Margin — entire. Average length 5.8 mm. Average width 4.1 mm. Upper surface glabrous, lower surface pubescent. Color — upper surface varies from 10Y 6/6 to 2.5GY 5/4. Lower surface varies from 7.5RP 3/4 to 10RP 4/6.

*Stamens.*—Average number per flower 40. Average filament length 12.7 mm. Filament color varies from N 9.5/ to 2.5RP 9/2. Anther color varies from 5R 4/8 to 7.5R 4/8.

*Pollen.*—Abundant, self fertile. Pollen color varies from 10YR 7/10 to 2.5Y 8/8.

*Pistil.*—Number — normally 1. Surface — glabrous. Average length 18.2 mm. Position of stigma — average of 1.8 mm above anthers. Color varies from 2.5GY 9/4 to 2.5GY 8/6.

*Fragrance.*—Slight to moderate aroma.

*Blooming period.*—Date of First Bloom Feb. 16, 2003. Date of Petal Fall Feb. 26, 2003, varies slightly with climatic conditions.

*Color.*—Varies from 5RP 8/6 to 7.5RP 7/8.
*Number flowers per flower bud.*—One.
*Pedicel.*—Average length 3.9 mm. Average width 1.2 mm. Color varies from 2.5GY 7/6 to 2.5GY 6/6.

Fruit:
*Maturity when described.*—Firm ripe.
*Date of first picking.*—May 18, 2003.
*Date of last picking.*—May 24, 2003. Varies slightly with climatic conditions.
*Size.*—Large. Average diameter axially 60.3 mm. Average transversely in suture plane 61.8 mm. Average weight 127.8 grams, varies slightly with fertility of the soil, amount of thinning and climatic conditions.
*Form.*—Globose.
*Suture.*—Smooth, nearly rounded.
*Ventral surface.*—Nearly smooth, very slightly lipped.
*Apex.*—Usually rounded, some fruit with slight tip.
*Base.*—Flat to slightly retuse.
*Cavity.*—Rounded to slightly elongated in suture plane. Average depth 7.0 mm. Average diameter 18.6 mm.

Stem:
*Size.*—Medium. Average length 6.9 mm. Average diameter 3.5 mm.
*Color.*—Varies from 2.5GY 7/8 to 5GY 6/8.

Flesh:
*Ripens.*—Evenly.
*Texture.*—Firm, holds firm on the tree 8 to 10 days after maturity shipping ripe.
*Fibers.*—Few, small, tender.
*Firmness.*—Firm, holds firm longer than most early maturing standard varieties.
*Aroma.*—Slight to moderate.
*Amydgalin.*—Undetected.
*Eating quality.*—Very good.
*Flavor.*—Very good, good balance between sugar and acid.
*Juice.*—Moderate amount, enhances flavor.
*Brix.*—Average Brix 14.7°, varies slightly with amount of fruit per tree and climatic conditions.
*Color.*—Varies from 5Y 9/2 to 7.5Y 9/2. Pit cavity varies from 5Y 8/4 to 7.5Y 7/4.

Skin:
*Thickness.*—Medium.
*Surface.*—Smooth.
*Down.*—Wanting.
*Tendency to crack.*—None.
*Color.*—Ground color varies from 5Y 9/4 to 7.5Y 9/4. Partially overspread with 5R 4/10 to 7.5R 4/8.
*Tenacity: Tenacious to flesh.*
*Astringency.*—None.

Stone:
*Type.*—Clingstone.
*Size.*—Large. Average length 35.3 mm. Average width 30.8 mm. Average thickness 21.5 mm.
*Form.*—Ovoid.
*Base.*—Usually flat, varies from flat to slightly rounded.
*Apex.*—Slightly pointed. Average length 2.5 mm.
*Surface.*—Pitted throughout, pits vary from round to slightly elongated. Ridges extend from base toward apex.
*Sides.*—Unequal, one side slightly larger, extending further from suture plane.
*Ridges.*—Relatively smooth with wide surface.
*Tendency to split.*—Very slight.
*Color.*—Varies from 7.5YR 7/6 to 5YR 5/8.

Kernal:
*Form.*—Ovate.
*Taste.*—Bitter.
*Viability.*—Poor, embryo only partially developed.
*Size.*—Large. Average length 15.0 mm. Average width 9.7 mm. Average depth 7.2 mm.
*Skin color.*—Varies from 5Y 9/2 to 5Y 9/4 when dry.

Use: Dessert. Market — local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described, characterized by its large size, vigorous, upright growth, with a low winter chilling requirement of approximately 250 hours at or below 45° F., and being a productive and regular bearer of early maturing, large size, white flesh, clingstone fruit with very good flavor and eating quality; the fruit is further characterized by having firm flesh with good handling and shipping quality.

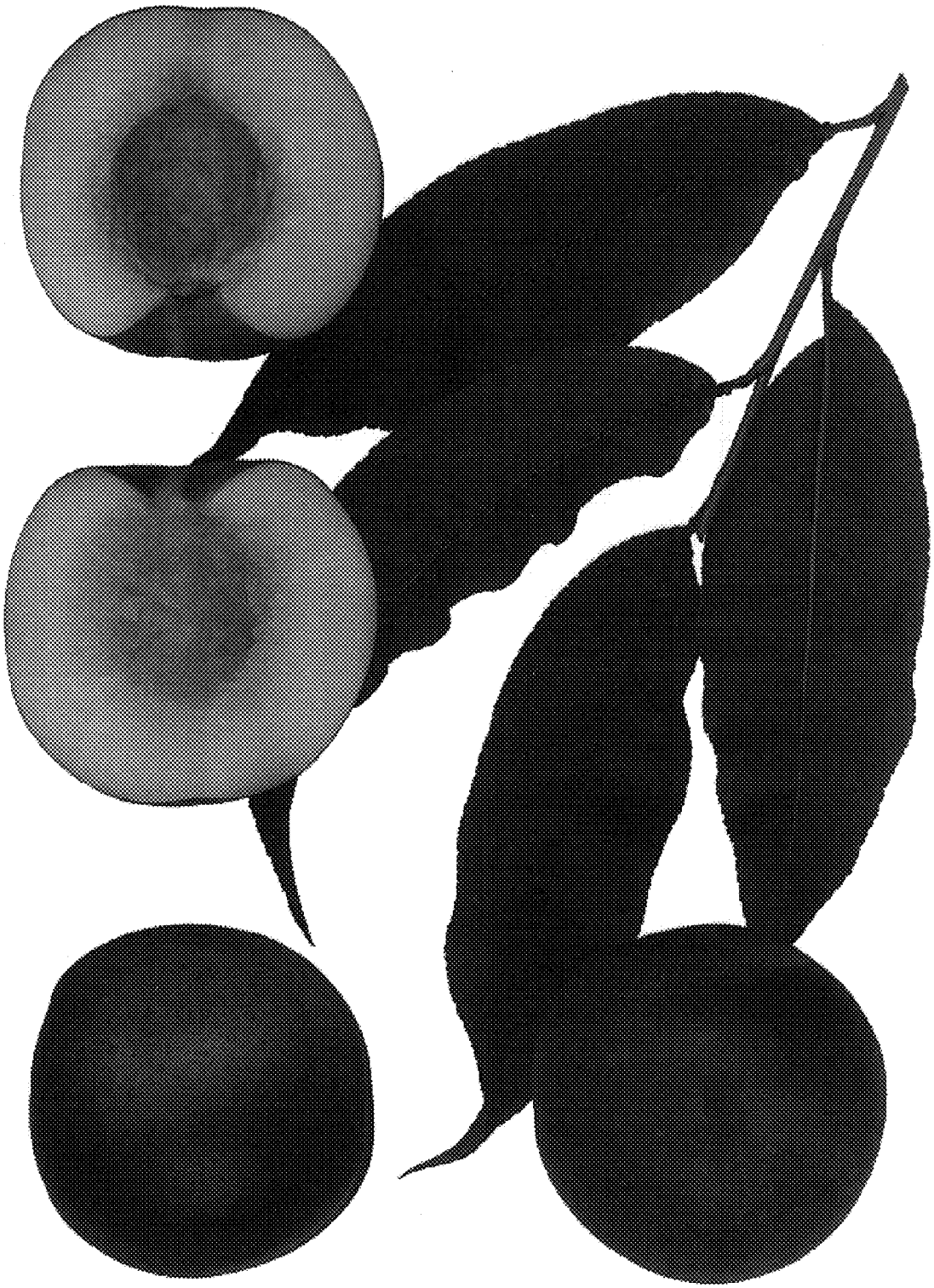

* * * * *